(12) United States Patent
Corson (10) Patent No.: US 7,269,518 B2
(45) Date of Patent: Sep. 11, 2007

(54) CHEMICAL ARRAY READING

(75) Inventor: John F. Corson, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 378 days.

(21) Appl. No.: 10/427,876

(22) Filed: Apr. 30, 2003

(65) Prior Publication Data

US 2004/0219536 A1    Nov. 4, 2004

(51) Int. Cl.
*G01N 31/00*    (2006.01)
(52) U.S. Cl. ..................................... 702/22; 435/287.2
(58) Field of Classification Search .................. 702/19, 702/22; 435/6
See application file for complete search history.

(56) References Cited

U.S. PATENT DOCUMENTS

| 6,185,030 | B1 | 2/2001 | Overbeck |
| 6,349,144 | B1 | 2/2002 | Shams |
| 6,406,849 | B1 | 6/2002 | Dorsel et al. |
| 6,591,196 | B1 | 7/2003 | Yakhini et al. |
| 6,993,172 | B2 | 1/2006 | Connell et al. |
| 2002/0160369 | A1 | 10/2002 | Dorsel et al. |
| 2002/0195554 | A1 | 12/2002 | Staton et al. |
| 2003/0036087 | A1* | 2/2003 | Kaushikkar et al. ........... 435/6 |

FOREIGN PATENT DOCUMENTS

| EP | 1 247 570 | 10/2002 |
| WO | WO99/08233 | 2/1999 |
| WO | WO 01/06395 | 1/2001 |

OTHER PUBLICATIONS

Wang et al. "Quantitative Quality Control in Microarray Image Processing and Data Acquisition," Nucleic Acids Research, vol. 29, No. 15 (2001) e75.*
Ramdas et al. "Comparative Evaluation of Laser-Based Microarray Scanner," BioTechniques (2001) vol. 31, pp. 546, 547, 550, 552.*
Pawlak et al. "Zeptosens' Protein Microarrays: A Novel High Performance Microarray Platform for Low Abundance Protein Analysis," Proteomics (Apr. 15, 2002) vol. 2, pp. 383-393.*
Cheung et al. "Making and Reading Microarrays," Nature Genetics Supplement (1999) vol. 21, pp. 15-19.*
Hentschel, Christian, "Fiber Optics Handbook", Hewlett-Packard Federal Republic of Germany, XP002305540, pp. 184-185.
Atilent G2566AA Feature Extraction Software User Manual, Fifth Edition, Sep. 2002, 144 pages.
Hentschel, Christian, "Fiber Optics Handbook", Hewlett-Packard Federal Republic of Germany, XP002305540, pp. 184-185, 1988.

* cited by examiner

*Primary Examiner*—John S. Brusca
*Assistant Examiner*—Jerry Lin (57) ABSTRACT

A method in which a chemical array is read on an array reader and the results saved in a memory linked with a performance characteristic of the array reader. Alternatively or additionally results from reading an array and a linked performance characteristic of a reader which performed the reading are retrieved from a memory. Computer program products and apparatus are also provided.

23 Claims, 3 Drawing Sheets

CHEMICAL ARRAY READING

FIELD OF THE INVENTION

This invention relates to arrays, particularly polynucleotide arrays such as DNA arrays, which are useful in diagnostic, screening, gene expression analysis, and other applications.

BACKGROUND OF THE INVENTION

Biopolymer arrays such as polynucleotide arrays (for example, DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers onto a substrate, or by in situ synthesis methods. The in situ fabrication methods include those described in U.S. Pat. No. 5,449,754 for synthesizing peptide arrays, and in U.S. Pat. No. 6,180,351 and WO 98/41531 and the references cited therein for synthesizing polynucleotide arrays. Further details of fabricating biopolymer arrays are described in U.S. Pat. Nos. 6,242,266, 6,232,072, 6,180,351, and 6,171,797. Other techniques for fabricating biopolymer arrays include known light directed synthesis techniques.

In array fabrication, the probes formed at each feature usually are expensive. Additionally, sample quantities available for testing are usually also very small and it is therefore desirable to simultaneously test the same sample against a large number of different probes on an array. These conditions make it desirable to produce arrays with large numbers of very small (for example, in the range of tens or one or two hundred microns), closely spaced features (for example many thousands of features). After an array has been exposed to a sample, the array is read with a reading apparatus (such as an array "scanner"), which detects the signals (such as a fluorescence pattern) from the array features. Such a reader should typically have a very fine resolution (for example, in the range of five to twenty microns).

The signal image resulting from reading the array can then be digitally processed to evaluate which regions (pixels) of read data belong to a given feature as well as the total signal strength from each of the features. The foregoing steps, separately or collectively, are referred to as "feature extraction". However, the signal in the image for any particular feature may be very low. Additionally, the results obtained by an array reader have inherent limitations governed by the reader's performance characteristics which affect how the read results are interpreted. For example, a low accuracy in a detected signal (as may result from high noise in the reader) may lead a user who is trying to interpret read results from an array (or software performing such a task) to conclude that the result (in the form of a detected signal) from a particular feature is unreliable where the detected signal from that feature is already low. This may lead to discarding the read result from that particular feature. The present invention recognizes though, that often results from reading chemical arrays are shared for others to evaluate. However, as the present invention further recognizes, shared results alone without an understanding of the performance characteristics of the reader which obtained them can lead to a misinterpretation of those results. For example, a user in the previous example having only the results from the reading, would not know that the result from the low signal feature should be discarded. This can lead to misinterpretation of the results from the read array with serious consequences in research or diagnosis.

The present invention recognizes then that it would be desirable to ensure that one or more performance characteristics of a chemical array reader are readily available along with the results from reading an array on that reader.

SUMMARY OF THE INVENTION

The present invention then, provides in one aspect a method which includes reading a chemical array on an array reader and saving the results in a memory linked with a performance characteristic of the array reader. Alternatively or additionally, the method may include retrieving from a memory the results from reading an array and a linked performance characteristic of a reader which performed the reading.

The present invention further provides an array reading system which includes a chemical array reader, and also includes a processor which receives read signals from the reader and executes a method of the present invention. In a still further aspect, the present invention provides a computer program product including a computer readable medium carrying a computer program code which performs a method of the present invention.

Different embodiments of the present invention can provide any one or more of the following or other useful benefits. For example, one or more performance characteristics of a chemical array reader are readily available along with the results from reading an array on that reader. This can reduce misinterpretation of the results from the array reading which might otherwise occur in the absence of the one or more array reader performance characteristics.

BRIEF DESCRIPTION OF THE DRAWINGS

Embodiments of the invention will now be described with reference to the following drawings in which.

To facilitate understanding, identical reference numerals have been used, where practical, to designate the same elements which are common to different figures. Drawings are not necessarily to scale. Throughout this application any different members of a generic class may have the same reference number followed by different letters (for example, arrays 12a, 12b, 12c, and 12d may generically be referenced as "arrays 12")

DETAILED DESCRIPTION OF EMBODIMENTS OF THE INVENTION

Throughout the present application, unless a contrary intention appears, the following terms refer to the indicated characteristics.

A "biopolymer" is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. Specifically, a "biopolymer" includes DNA (including cDNA), RNA and oligonucleotides, regardless of the source.

A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides.

An "oligonucleotide" generally refers to a nucleotide multimer of about 10 to 100 nucleotides in length, while a "polynucleotide" includes a nucleotide multimer having any number of nucleotides.

A chemical "array", unless a contrary intention appears, includes any one, two or three-dimensional arrangement of addressable regions bearing a particular chemical moiety or moieties (for example, biopolymers such as polynucleotide sequences) associated with that region. Each region may extend into a third dimension in the case where the substrate is porous while not having any substantial third dimension measurement (thickness) in the case where the substrate is non-porous. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). An array feature is generally homogenous in composition and concentration and the features may be separated by intervening spaces (although arrays without such separation can be fabricated). In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other).

An "array layout" or "array characteristics", refers to one or more physical, chemical or biological characteristics of the array, such as positioning of some or all the features within the array and on a substrate, one or more feature dimensions, or some indication of an identity or function (for example, chemical or biological) of a moiety at a given location, or how the array should be handled (for example, conditions under which the array is exposed to a sample, or array reading specifications or controls following sample exposure).

"Hybridizing" and "binding", with respect to polynucleotides, are used interchangeably.

A "plastic" is any synthetic organic polymer of high molecular weight (for example at least 1,000 grams/mole, or even at least 10,000 or 100,000 grams/mole.

"Flexible" with reference to a substrate or substrate web, references that the substrate can be bent 180 degrees around a roller of less than 1.25 cm in radius. The substrate can be so bent and straightened repeatedly in either direction at least 100 times without failure (for example, cracking) or plastic deformation. This bending must be within the elastic limits of the material. The foregoing test for flexibility is performed at a temperature of 20° C.

A "web" references a long continuous piece of substrate material having a length greater than a width. For example, the web length to width ratio may be at least 5/1, 10/1, 50/1, 100/1, 200/1, or 500/1, or even at least 1000/1.

When one item is indicated as being "remote" from another, this is referenced that the two items are at least in different buildings, and may be at least one mile, ten miles, or at least one hundred miles apart. When different items are indicated as being "local" to each other, they are at least in the same building and may be in the same room of a building. "Communicating", "transmitting" and the like, reference conveying data representing information as electrical or optical signals over a suitable communication channel (for example, a private or public network, wired, optical fiber, wireless radio or satellite, or otherwise). Any communication or transmission can be between devices which are local or remote from one another. "Forwarding" an item refers to any means of getting that item from one location to the next, whether by physically transporting that item or using other known methods (where that is possible) and includes, at least in the case of data, physically transporting a medium carrying the data or communicating the data over a communication channel (including electrical, optical, or wireless). "Receiving" something means it is obtained by any possible means, such as delivery of a physical item (for example, an array or array carrying package). When information is received it may be obtained as data as a result of a transmission (such as by electrical or optical signals over any communication channel of a type mentioned herein), or it may be obtained as electrical or optical signals from reading some other medium (such as a magnetic, optical, or solid state storage device) carrying the information. However, when information is received from a communication it is received as a result of a transmission of that information from elsewhere (local or remote).

When two items are "associated" with one another they are provided in such a way that one unambiguously references the other. In particular, an array identifier can be associated with an array by being on the same substrate that carries the array or on or in a package or kit carrying the array. Items of data is "linked" to another in memory when a same data input (for example, filename or directory name or search term) retrieves both (in a same file or not) or an input of one item retrieves the other. In particular, when an array layout is "linked" with an identifier for that array, then an input of the identifier into a processor which accesses a memory carrying the linked array layout unambiguously retrieves the array layout for that array. Similarly, when results read from an array are "linked" with one or more array reader characteristics, a retrieval of the results (such as by filename, directory name, or linked array identifier) also retrieves the one or more reader characteristics.

A "computer", "processor" or "processing unit" are used interchangeably and each references any combination of hardware or software which can control components as required to execute recited steps and includes. For example a computer, processor, or processor unit includes a general purpose digital microprocessor suitably programmed to perform all of the steps required of it, or any hardware or software combination which will perform those or equivalent steps. Programming may be accomplished, for example, from a computer readable medium carrying necessary program code or by communication from a remote location.

A "memory" or "memory unit" refers to any device which can store information for retrieval as signals by a processor, and may include magnetic, optical, or solid state memory devices. A memory or memory unit may have more than one physical memory device (for example, a memory may have multiple memory devices such as multiple hard drives).

An array "unit" may be the array plus only a substrate on which the array is deposited, although the assembly may be in the form of a package which includes other features (such as a housing with a chamber). "Array unit" may be used interchangeably with "array assembly".

A "signal image" is acquired by reading, such an in a chemical array reader, a signal from a sample, such as an array. A signal image may exist solely as a signal data in a memory but may be presented on a display or some other device for human viewing if desired.

"Performance characteristic" means information which describes how or how well a chemical array reader obtained a result from reading and can be used to define the limits of relevance and/or confidence that the reader introduces into the data-set. A performance characteristic of a reader defines a characteristic of the reading system as a whole and not a characteristic of an individual subsystems (for an example see below in the definition of "lower limit of detection"). A performance characteristic can include any one or more of: responsivity; accuracy in detected signal or ratios of detected signals in different channels; or sample parameter. Performance characteristics are not affected by the array being read (although they can be different for different read arrays as a result of a different setting in the reader for the different arrays).

"Responsivity" is the extent or degree to which a reader responds to a signal or signals which it is detecting. Responsivity then includes any one or more of: a detection limit of the reader (for example, an upper or lower limit of detection), variations of detected signal value per actual signal value over a space to be read (for example, signal inhomogeneities over a field of view), channel cross-talk. Responsivity does not include "scale factor".

"Scale factor" is the detected signal value per actual signal (for example, detected signal value per emitting species in a region from which signal is being detected, sometimes referenced as "scale factor").

"Lower limit of detection" refers to the lowest signal level for a feature such that the feature can be confidently differentiated from the noise. This criterion of 'differentiablity' can, for example, be that the ratio of the signal level to the noise be greater than 3. Noise in this context should be understood to mean the combined noise of the system for a signal near the lower limit of detection. This noise can contain contributions from various sources of noise (electronic noise, detector noise, noise in the light from fluorescence of the array substrate). However, the 'noise' here is the combination of all such noises due to individual sub-systems. This is an important distinction because it is this combined noise that is most useful for the user seeking to interpret the meaning of the data (not any one individual noise source). Furthermore, the lower limit of detection assume certain parameters: size of feature to be detected, fluorescence amount of the array substrate used, signal to noise ratio assumed to be the limit, etc.

"Accuracy" refers to limitations in the data due to error or uncertainty in measurement (for example, noise or other uncertainty in detected signal or ratios of detected signals in different channels). This may be given in terms of a signal to noise ratio for a given signal level. Since the noise may vary as a function of the signal, this characteristic may be included for a number of signal levels in the dynamic range of the reader between the lower and upper limits of detection.

"Channel cross-talk" or "cross-talk" in a channel refers to the signal in that channel of a multi-channel array reader actually attributable to signal from another channel. Different "channels" refer to the different electrical signal paths along which different signals from the array reading pass.

"Sample parameter" refers to a physical characteristic of a sample (such as an array or uniform test slide being read). For example this could include size of feature to be detected, fluorescence amount of the array substrate read, flatness characteristics of any sample used to measure the variations of detected signal value per actual signal value over a space to be read, or the flatness of the array being read.

It will also be appreciated that throughout the present application, that words such as "front", "back", "top", "upper", and "lower" are used in a relative sense only.

"May" refers to optionally.

Any recited method can be carried out in the order of events recited or in any other order which is logically possible. Reference to a singular item, includes the possibility that there are plural of the same item present. All patents and other references cited in this application, are incorporated into this application by reference except insofar as anything in those patents or references, including definitions, conflicts with anything in the present application (in which case the present application is to prevail).

In methods of the present invention the reader may read the chemical array by detecting optical signals, such as that resulting from chemiluminescence, electroluminescence, or light emitted in response to illumination (such as fluorescence). The performance characteristic may be any one or more of reader accuracy, responsivity, or sample parameter. Methods of the present invention may additionally include reading an array identifier associated with the chemical array (for example, a bar code on an array substrate). In this case the read results and performance characteristic of the array reader may both be saved in the memory linked with the identifier.

Additionally, the performance characteristic may be retrieved from a memory in which it was earlier saved (such as from an earlier measuring of the performance characteristic), prior to the saving with the linked results from the reading.

Where the method includes retrieving results and a performance characteristic, the method may additionally include processing the retrieved results using the retrieved performance characteristic. For example, a result from one or more features may be rejected based on the retrieved performance characteristic.

A chemical array reading system of the present invention may include, in addition to an array reader having a detector and the previously mentioned processor, also include a memory in which the read results and performance characteristic may be saved. Additionally, such a system may also include an identifier reader to read an identifier associated with the array. Both the read results and the read identifier may be communicated to the processor.

Figure 1:
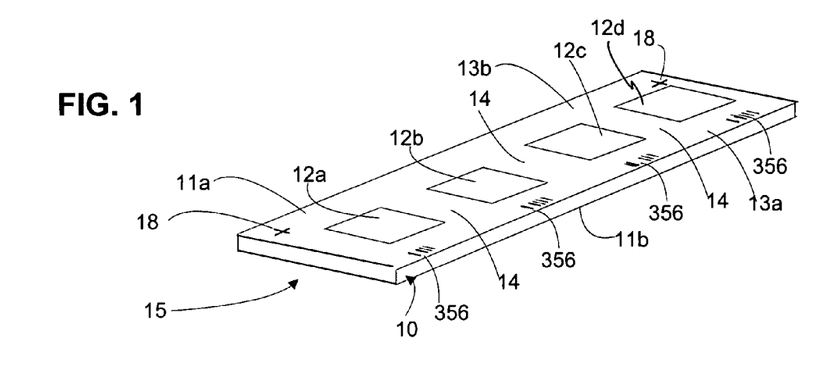
FIG. 1 illustrates a substrate carrying multiple arrays, such as may be read by a method of the present invention.
Figure 2:
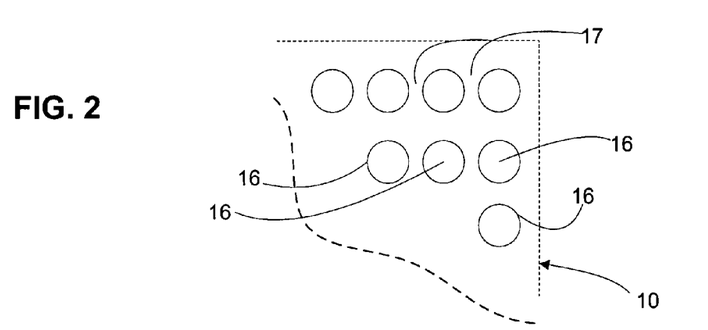
FIG. 2 is an enlarged view of a portion of FIG. 2 showing multiple spots or features of one array.
Figure 3:
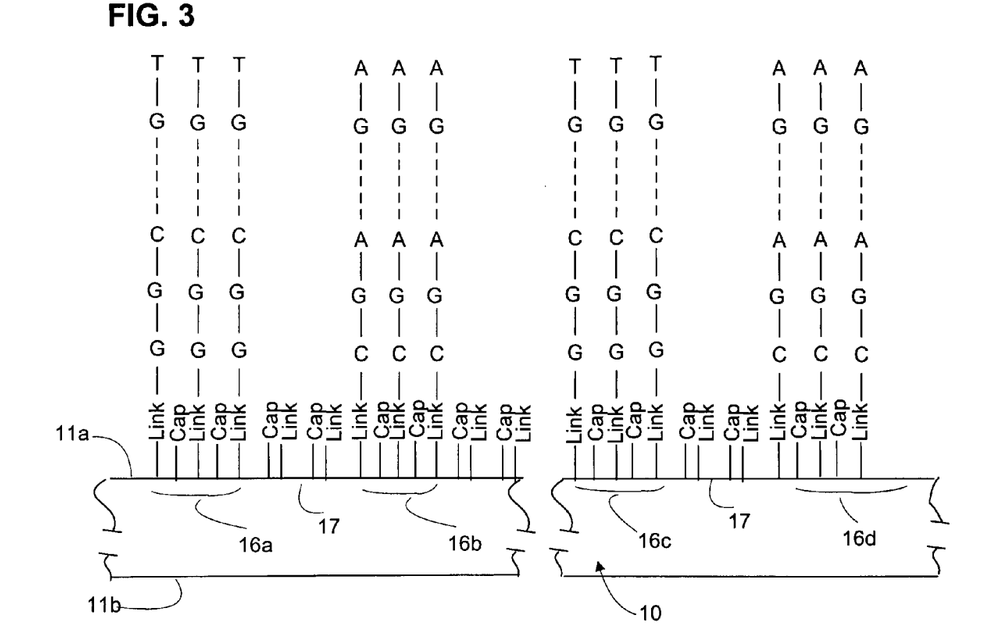
FIG. 3 is an enlarged illustration of a portion of the substrate of FIG. 1.

Referring now to FIGS. 1-3, an array assembly 15 (which may also be referenced as an "array unit") includes arrays 12 which may be read to obtain an array image used in methods of the present invention. Substrate 10 may also be in the form of an a rigid substrate 10 (for example, a transparent non-porous material such as glass or silica) of limited length, carrying one or more arrays 12 disposed along a front surface 11a of substrate 10 and separated by inter-array areas 14. Alternatively, substrate 10 can be flexible (such as a flexible web). The substrate may be of one material or of multi-layer construction. Substrate 10 is typically non-porous, and may be smooth and planar, or have irregularities, such as depressions or elevations (although irregular substrate surfaces may make reading of the exposed array more difficult). However, even a flat planar substrate 10 may have small irregularities in its shape (for example, front side 11a may be slightly bent or bowed). A back side 11b of substrate 10 does not carry any arrays 12. The arrays on substrate 10 can be designed for testing against any type of sample, whether: a trial sample; reference sample; a combination of the foregoing; or a known mixture of polynucleotides, proteins, polysaccharides and the like (in which case the arrays may be composed of features carrying unknown sequences to be evaluated). While four arrays 12 are shown in FIG. 1, it will be understood that substrate 10 may use any number of desired arrays 12 such as at least one, two, five, ten, twenty, fifty, or one hundred (or even at least five hundred, one thousand, or at least three thousand). When more than one array 12 is present they may be arranged end to end along the lengthwise direction of substrate 10. Depending upon intended use, any or all of arrays 12 may be the same or different from one another and each will contain multiple spots or features 16 of biopolymers in the form of polynucleotides.

A typical array 12 may contain more than: ten, one hundred, one thousand, or ten thousand features. For example, features may have widths (that is, diameter, for a round spot) in the range from a 10 µm to 1.0 cm. In other embodiments each feature may have a width in the range of 1.0 µm to 1.0 mm, usually 5.0 82 m to 500 µm, and more usually 10 µm to 200 µm. Non-round features may have area ranges equivalent to that of circular features with the foregoing width (diameter) ranges. At least some, or all, of the features are of different compositions (for example, when any repeats of each feature of the same composition are excluded, the remaining features may account for at least 5%, 10%, or 20% of the total number of features). The features may have a maximum dimension of between 20 (or 50) to 100 (or 80) microns and be spaced apart by less than 130 microns (or by less than 100 or 50 microns). Various feature densities on the substrate surface are possible. For example, features having a maximum dimension greater than any of the foregoing figures may be present on the surface of at least 30 features/mm$^2$, 40 features/mm$^2$, or 60 features/mm$^2$. While round features 16 are shown, various other feature shapes are possible (such as elliptical). The features 16 may also be arranged in other configurations (for example, circular) rather than the rectilinear grid illustrated. Similarly, arrays 12 on a same substrate 10 need not be laid out in a linear configuration.

Each array 12 may cover an area of less than 100 cm$^2$, or even less than 50 cm$^2$, 10 cm$^2$ or 1 cm$^2$. In many embodiments, particularly when substrate 10 is rigid, it may be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. When substrate 10 is flexible, it may be of various lengths including at least 1 m, at least 2 m, or at least 5 m (or even at least 10 m). With arrays that are read by detecting fluorescence, the substrate 10 may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

In the case where arrays 12 are formed by the conventional in situ or deposition of previously obtained moieties, as described above, by depositing for each feature a droplet of reagent in each cycle such as by using a pulse jet such as an inkjet type head, interfeature areas 17 will typically be present which do not carry any polynucleotide. It will be appreciated though, that the interfeature areas 17 could be of various sizes and configurations. Further, such interfeature areas 17 need not be present at all (such as when arrays are fabricated using light directed synthesis techniques). Where interfeature areas 17 are present, the features 16 may be spaced apart by a distance greater than 0 and less than 70%, 60% 50%, 25%, or 10% of a maximum dimension of the feature. Each feature 16 carries a predetermined polynucleotide (which includes the possibility of mixtures of polynucleotides). As per usual, A, C, G, T represent the usual four nucleotides. "Link" (see FIG. 3 in particular) represents a linking agent (molecule) covalently bound to the front surface and a first nucleotide, as provided by a method of the present invention and as further described below. The Link serves to functionalize the surface for binding by the first nucleotide during the in situ process. "Cap" represents a capping agent. The Link may be any of the "second silanes" referenced in U.S. Pat. No. 6,444,268 while the Cap may be any of the "first silanes" in that patent. However, different linking layer compositions than those silanes could be used. As already mentioned, the foregoing patents are incorporated herein by reference, including for example the details of the linking layer compositions used therein.

Substrate 10 also has one or more identifiers 356 each in the form of a bar code. Identifiers 356 may be associated with an array by being: directly printed onto the substrate 10 or a housing (not shown) carrying substrate 10; printed onto labels attached to substrate 10 or a housing carrying substrate 10; contained in a memory (for example, a solid state memory) attached to substrate 10 or a housing carrying substrate 10; or be provided on a printed label or paper or some other medium or in a memory, any of which is received in or on a same package containing the array unit 15 (and therefore also containing substrate 10). Identifiers such as other optical or magnetic identifiers could be used instead of bar codes, and which will carry the information discussed below. Each identifier may be associated with its corresponding array by being positioned adjacent that array 12 on the same substrate 10. However, this need not be the case and identifiers 356 can be positioned elsewhere on substrate 10 if some other means of associating each identifier 356 with its corresponding array is provided (for example, by relative physical locations). Further, a single identifier might be provided which is associated with more than one array 12 on a same substrate 10 and such one or more identifiers may be positioned on a leading or trailing end of substrate 10. Each identifier 356 may also be associated with an array by being in or on a same package or kit which contained by the array and is received by a user. The substrate may further have one or more fiducial marks 18 for alignment purposes during array fabrication or reading.

FIGS. 2 and 3 illustrate ideal features 16 of an array 12 where the actual features formed are the same as the target (or "aim") features, with each feature 16 being uniform in shape, size and composition, and the features being regularly spaced. Such ideally shaped features may not always be possible to obtain but this is not critical in any event. Suitable drop deposition methods for fabricating arrays 12 include those as described in U.S. Pat. Nos. 6,180,351, 6,242,266, 6,306,599, and 6,420,180. As mentioned above, the foregoing references are incorporated herein by reference particularly as relates to the in situ fabrication apparatus and methods disclosed therein. Alternatively, arrays 12 can be fabricated by known light directed synthesis methods.

Figure 4:
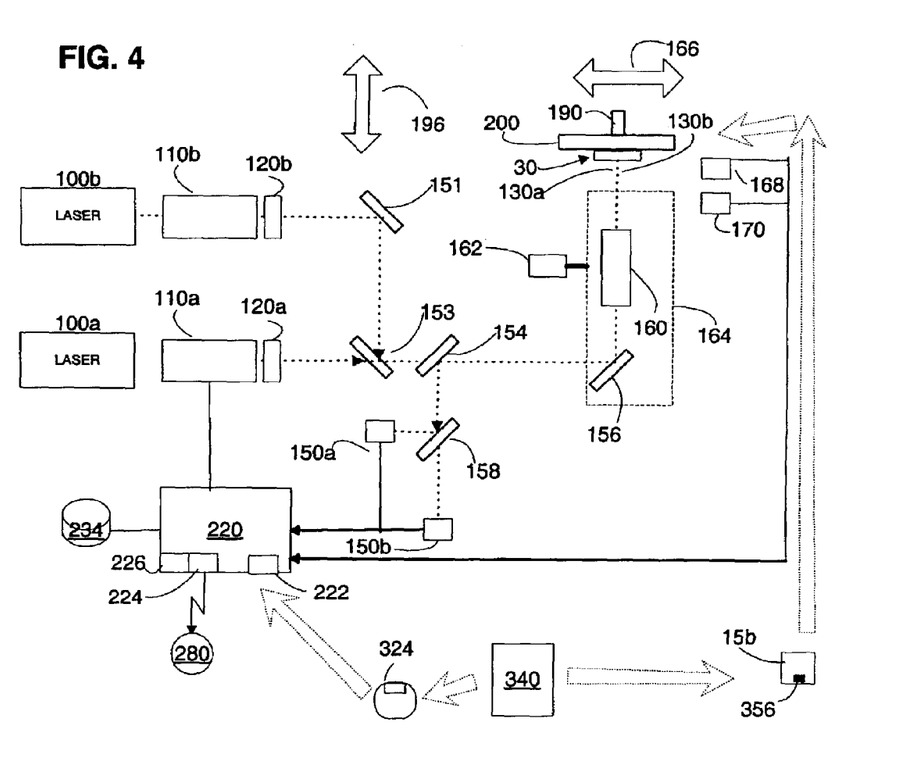
FIG. 4 is a schematic diagram of an array reader system of the present invention.

Referring now to FIG. 4, an array reading system of the present invention is shown. FIG. 4 illustrates in more detail certain components of the array reader system, particularly components of the array reader itself (which may be generally referenced as an array "scanner"). In FIG. 4, a light system provides coherent light from a laser 100 which passes through an electro-optic modulator (EOM) 110 with attached polarizer 120. Each laser 100a, 100b may be of different wavelength (for example, laser 100a providing red light with a peak emission at 630 nm, and laser 100b providing green light with a peak emission at 530 nm) and each has its own corresponding EOM 110a, 110b and polarizer 120a, 120b. The resulting light beams are coherent and monochromatic.

The red interrogating light beam originating from laser 100a is directed along path 130a while the interrogating green beam originating from laser 100b is directed along respective paths 130b. Light is directed along all of the paths 130a, 130b by means of full mirror 151, dichroic mirror 153, and full mirror 156 onto two different locations of an array being read (namely an array 12 of an array unit 15 mounted on holder 200), using optical components in beam focuser 160. Note though that FIG. 4 shows the paths 130a, 130b of the two beams as being coincident up until the position of a mirror 158, for the sake of simplicity. The angle of separation of the beams may be such that each interrogating light beam is directed along a corresponding path 130a, 130b toward front surface 11a at an angle equal that is greater than or equal to 0 degrees and up to 45 degrees to a normal to the back surface (for example less than 1 degree, such as 0.5 degrees). Such an arrangement allows the two interrogating light beams to pass through the same optical system while reducing saturation of fluorescent labels at features 16 as well as channel cross-talk. A control signal in the form of a variable voltage applied to each corresponding EOM 110a, 110b by the controller (CU) 220, changes the polarization of the exiting light which is thus more or less attenuated by the corresponding polarizer 120a, 120b. Controller 220 may be or include a suitably programmed processor. Thus, each EOM 110 and corresponding polarizer 120 together act as a variable optical attenuator which can alter the power density of the light exiting from the attenuator. Hence each EOM 110 alters the power density of the interrogating light spot originating from one of lasers.

Each of the two beams provided on paths 130a, 130b then provide two spatially separated spots on an array 12 of an array unit 15 mounted on holder 200. These may be focused on front surface 11a directly without passing through substrate 10 when the array is being read with front surface 11a facing beam focuser 160 (that is, facing down in FIG. 4), or may be focused on front surface 11a after first passing through substrate 10 when the array is being read with front surface 11a facing away from beam focuser 160 (that is, facing up in FIG. 4). Various patterns for the spot separation can be used but the pattern of spots relative to one another will generally remain fixed unless independent optics were provided for the different beam paths 130. Note also that with the foregoing configuration the longer wavelength red light will generally be positioned to illuminate a given region of a feature before a spot of the shorter green light also tending to reduce triplet saturation as described in U.S. Pat. No. 6,320,196. As already mentioned, that patent is incorporated herein by reference in relation to the reading methods described therein.

Light emitted, in particular fluorescence, at two different wavelengths (for example, green and red light) from regions illuminated by the green and red interrogating light spots, in response to the interrogating light, is imaged using the same optics in focuser/scanner 160, and is reflected off mirror 156 and dichroic 154. The two different wavelengths are separated by a further dichroic mirror 158. There will be two paths of detection resulting from the spaced two interrogating light spots. As already mentioned though, for the sake of clarity these are only shown as one path in FIG. 4 up until mirror 158. Dichroic mirror 158 will direct red fluorescent light resulting from one interrogating light spot onto a detector 150a, while green fluorescent light resulting from another interrogating light spot will be directed onto detector 150b. More optical components (not shown) may be used between the dichroic and each of the two detectors 150 (such as lenses, pinholes, filters, fibers etc.) and each detector 150 may be of various different types (e.g. a photo-multiplier tube (PMT) or a CCD or an avalanche photodiode (APD)). All of the optical components through which light emitted from an array 12 in response to the illuminating laser light, passes to the two detectors 150, together with those detectors, form a detection system. This detection system has a fixed focal plane on the array 12 being read for a given position of the autofocus system (that is, in direction 196).

Instead of using dichroic 158, one can also use a design that images the different scanning spots onto different light-guiding fibers that then guide the signal from each one of these to a different detector. Such an arrangement for two scanning spots is described in U.S. Pat. No. 6,320,196.

In order to raster scan red and green interrogating light spots, the scanner is provided with a scan system. In this manner, each of the multiple features 16 of the array is read, with each read feature containing multiple pixels (for example, more than five, ten, or twenty). This can be accomplished by providing a housing 164 containing mirror 158 and focuser 160, which housing 164 can be moved in a first direction along a line (that is, from left to right or the reverse as viewed in FIG. 4) by a transporter 162. The second direction 192 of scanning (line transitioning) can be provided by second transporter which may include a motor and lead screw or belt (not shown) to move holder 200 along one or more tracks. The second transporter may use a same or different actuator components to accomplish coarse (a larger number of lines) movement and finer movement (a smaller number of lines). The reader of FIG. 4 may further include a machine reader 226 which reads an identifier 356 from an array unit 30 and provides the read identifier to controller 220. When identifier 356 is in the form of a bar code, that reader 226 may be a suitable bar code reader 168. Of course, other scanning patterns could be used.

An autofocus detector 170 is also provided to sense any offset between different locations on array 12 when in the reading position, and a determined position of the focal plane of the detection system. An autofocus system includes detector 170, processor 220, and a motorized adjuster to move holder in the direction of arrow 196 (which may be referenced as a "z-axis" direction). A suitable chemical array autofocus system is described in U.S. Pat. No. 6,486,457.

Controller 220 of the apparatus is connected to receive signals from the detectors 150a, 150b. Each detector is part of another detection "channel". The signals in each channel are obtained at each of the two detected wavelengths from emitted light for each scanned pixel on array 12 when at the reading position mounted in holder 200. Controller 220 also receives the signal from autofocus offset detector 170, and provides the control signal to EOM 110, and controls the scan system. Controller 220 may also analyze, store, and/or output data relating to emitted signals received from detectors 150a, 150b in a known manner, as well as control the sensitivities of one or more of the four detectors.

Controller 220 may include a computer in the form of a programmable digital processor, and include a media reader/writer 222 which can read and write to a portable removable memory 324 (such as a magnetic or optical disk, or solid state memory), and a communication module 224 which can communicate over a communication channel 280 (such as a network, for example the internet, a telephone network, a WAN or LAN, or satellite link) with a remote site (such as a database at which information relating to array unit 30 may be stored in association with the identifier 40). Controller 220 is suitably programmed to execute all of the steps required by it during operation of the apparatus, as discussed further below. Controller 220 can be programmed from any computer readable medium carrying a suitable computer program. For example, such a medium can be a memory device read by writer/reader 222 or may be programmed from a remote location through communication channel 280. Alternatively, controller 220 may be any hardware or hardware/software combination which can execute those steps.

The components of the reader system may all be contained within the same housing of a single same apparatus, or control unit 220 may be a separate unit such as a standalone computer with the appropriate peripherals. The reader system of FIG. 4 may further include a display and a user input device (neither shown) communicating with control unit 220. One particular reader system is disclosed in U.S. Pat. No. 6,406,849. One particular reader system that may be used is the AGILENT MICROARRAY SCANNER manufactured by Agilent Technologies, Palo Alto, Calif.

In one mode of operation a user may receive a package 340 at a location of the reader system of FIG. 4 (or another location remote or not to that reader system). Package 340 contains an array unit and optionally a portable memory 324 (such as a disk) in package 340 only. A "package" in this context is one or more array units optionally with other items, all held together (such as by a common wrapping or protective cover or binding). Normally the common wrapping will also be a protective cover (such as a common wrapping or box) which will provide additional protection to the substrate 10 from exposure to the external environment. In the case of just a single array unit the package may be that array unit with some protective covering over the array 12 and substrate 10 (which protective cover may or may not be an additional part of the array unit 15 itself).

The user exposes each array 12 on the array unit 15 to a liquid aqueous sample, for example a test sample derived from a human or other organism or source. Samples can be prepared for exposure to an array 15 using methods such as described in U.S. Pat. Nos. 6,235,483 or 6,132,997. After a suitable time of exposure, the array may then be washed with buffer then water, and dried following washing then inserted into a scanner for reading in a manner already described. Drying may be accomplished using any suitable drying method and conditions which will not decompose the probes and their bound targets, such as any suitable one or more of: air drying at room temperature or raised temperature; reduced pressure; centrifuging; or exposure to a dry unreactive gas stream (such as dry nitrogen).

Figure 5:
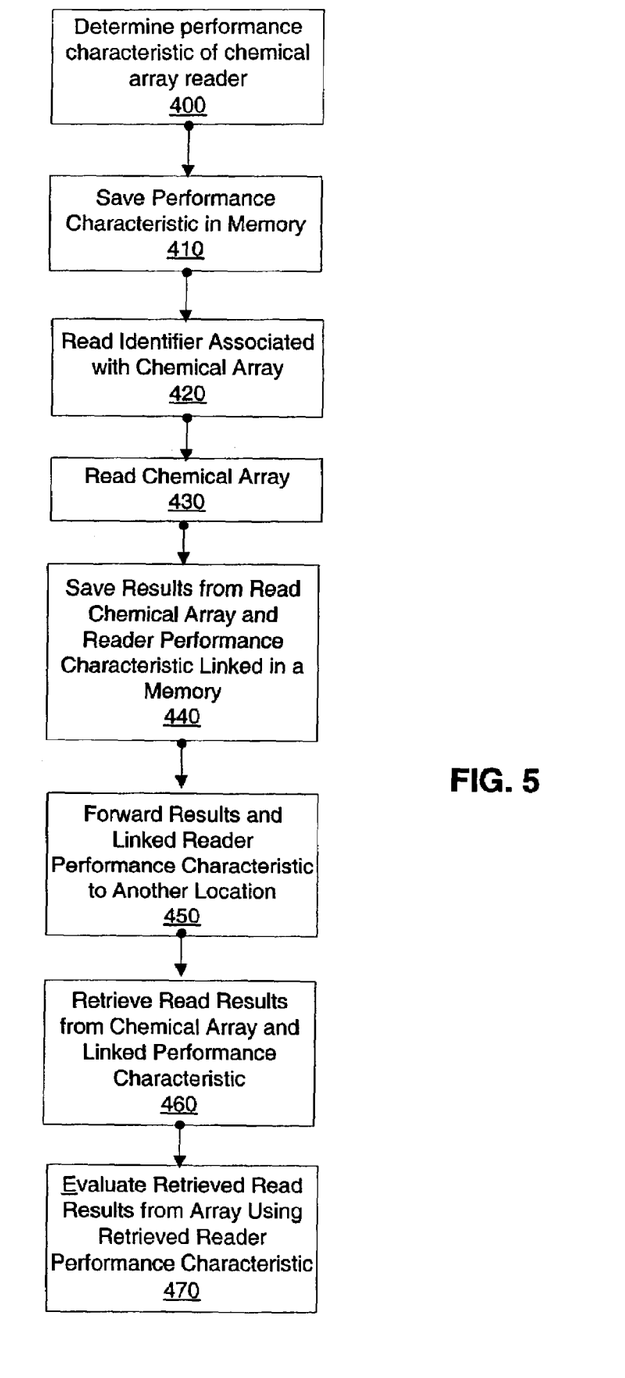
FIG. 5 is a flowchart illustrating methods of the present invention.

Some methods of the present invention which may be operated in conjunction with an apparatus of FIG. 4 or with another apparatus, are illustrated in FIG. 5. In the following description, numbers in parentheses refer to processes in FIG. 5. In particular, a user may initially determine (400) a performance characteristic of an array reader system of FIG. 4. Methods for determining performance characteristics of such a system may be the same or similar to those which may be used in determining performance characteristics of other optical systems, such as spectrophotometers. Such methods are described in Handbook of Biological Confocal Microscopy $2^{nd}$ edition—Edited by James B. Pawley—Plenum Press—(1995). For example, noise can be determined by measuring variations in repeated detection of a constant signal source in holder 200. To the extent that the signal of a certain sample varies from one measurement to another it represents noise in the measurement and can be used to determine an accuracy (defined above to include a signal to noise ratio). The upper detection limit can be determined by measuring a series of known signal reference sources in holder 200 of increasing amplitude and determining the signal level where the signal output saturates. The lower limit of detection can be measured by determining the noise floor. The noise floor is the level of noise in the absence of signal (or with a low signal near the limit of detection). The lower limit of detection is usually a signal that is a multiple of this amount of noise (often a multiple of three). Scale factor can be similarly determined using a known reference signal source in holder 200 with only a single species of dye and recording the detected signal in all of the channels not intended to detect signal from that dye. Variations in view field non-uniformities can be determined as described in U.S. Patent Application Publication No. 20040218793 titled "Feature Locations in Array Reading" by Corson, et al., filed the same date as the present application. The determined performance characteristics can be saved (410) in memory 234. Alternatively, the performance characteristics saved in the memory 234 may be previously provided by a manufacturer of the array reader system of FIG. 4.

An identifier 356 associated with array 12 may then be read (420) by reader 226 (such as by swiping the code 356 past reader 226) and the array also placed in holder 200 for reading (430). The previously saved reader performance characteristic is retrieved from memory and the results from reading saved (440) in memory 234 linked together along with the read array identifier 356. The saved and linked reader performance characteristic, read results, and array identifier 356, may all be forwarded (450) to a remote or non-remote further location such as by transmission through communication channel 280 or saved on portable media 324 which is then forwarded by shipping to the remote or non-remote location, where any of them are received. Further, this reader performance characteristics can be included in the file header of the image file generated by the reader (often in the form of a .tiff file).

In any event, when it is desired to process the read results they may be retrieved (460) along with the linked reader performance characteristic and optionally the array identifier 356. Again, if processing will be at the same reader station of FIG. 4, they may all be retrieved from memory 234. If processing will be at another location (remote or not) from the array reader system of FIG. 4, they may be retrieved through communication channel 280 or from a received portable media 324. The read results may be processed by evaluating (470) them using the retrieved reader performance characteristic. For example, if a signal from pixels of a read feature 16 are all (or mostly) below an lower limit of detection characteristic of the array reader which read the array, it may be decided to ignore (reject) the result from that feature or at least flag it as suspect in any subsequent analysis. Similarly, if the signal from those pixels is within a predetermined range of reader responsivity, for example within a predetermined tolerance of a lower or upper detection limit, that feature result may again be ignored or flagged. The accuracy of the signal can be used to generate error bars or confidence intervals for the data. This can be done used standard statistical techniques well known to those skilled in the art. For example if the noise for a given signal level is recorded (i.e., in terms of a signal to noise ratio for a given signal level), then error bars determining a 3× standard deviation confidence interval can be added to the data points at that signal level. Also, scale factor may be used to determine the actual the number or concentration of signal emitting species in a feature from which signal is being detected. Further, cross-talk value between red and green channels of the array reader of FIG. 4 may be used to identify different detected red and green signals as actually being the same when they are within the cross-talk value.

Following the above, feature extraction can be performed using known methods, or those such as described in U.S. patent applications Ser. No. 10/077446 titled "Method And System For A Range Of Automatic, Semi-Automatic, And Manual Grid Finding During Feature Extraction From Molecular Array Data." and U.S. Pat. No. 6,591,196 titled "Method And System For Extracting Data From Surface Array Deposited Features," the relevant disclosures of which are incorporated by reference. Following or before feature extraction, details of the array layout can be retrieved using the read array identifier 356 in a manner similar to that described in U.S. Pat. No. 6,180,351. Any results of this processing may then be used to make an assessment if one or more targets are present in a sample to which the array was exposed, or whether an organism from which the sample was obtained exhibits a particular condition (for example, cancer). The processed results may be further forwarded or transmitted to a remote location at which they are received, and can be re-transmitted to elsewhere from that location as desired.

Various and modifications to the particular embodiments described above are, of course, possible. Accordingly, the present invention is not limited to the particular embodiments described in detail above.

What is claimed is:

1. A method comprising:
   (i) reading a chemical array on an array reader, wherein the chemical array comprises biopolymer features and was exposed to a sample, and saving results of the reading in a memory, wherein the saved results are linked with a performance characteristic of the array reader which performed the reading, and processing the saved results using the linked performance characteristic of the reader which performed the reading; or
   (ii) retrieving from a memory the results from reading an array, the results being linked with a performance characteristic of a reader which performed the reading, wherein the array comprises biopolymer features and was exposed to a sample, and processing the retrieved results using the retrieved performance characteristic of the reader which performed the reading; and, based on said processing, a human user who is interpreting the results of the reading assesses whether one or more targets is present in the sample or whether an organism from which the sample was obtained exhibits a particular condition,
   wherein the performance characteristic comprises one or more of a reader accuracy or a reader responsivity of the reader which performed the reading and wherein processing includes rejecting or flagging as suspect a result from one or more of the features based on a predetermined performance characteristic or generating error bars or confidence intervals for a result from one or more of the features.

2. A method according to claim 1 wherein in (i) the reader detects light emitted in response to illumination.

3. A method according to claim 1 wherein in (i) an array identifier associated with the chemical array is read; and wherein the read results and performance characteristic of the array reader are both saved in the memory linked with the identifier.

4. A method according to claim 2 wherein the reader includes a memory in which the performance characteristic is saved, the method additionally comprising retrieving the performance characteristic from the memory prior to the saving with the linked results from the reading.

5. A method according to claim 2 additionally comprising measuring the performance characteristic prior to the saving with the linked results from the reading.

6. A method according to claim 2 additionally wherein the performance characteristic comprises reader accuracy.

7. A method according to claim 2 additionally wherein the performance characteristic comprises reader responsivity.

8. A method according to claim 2 additionally wherein the performance characteristic comprises a sample parameter.

9. A method comprising forwarding the saved results and linked performance characteristic obtained by a method of claim 2 to a remote location.

10. A method comprising receiving the saved results and linked performance characteristic obtained by a method of claim 2 from a remote location.

11. A method according to claim 1 wherein the results from reading an array and a linked performance characteristic of a reader which performed the reading are retrieved from a memory.

12. A method according to claim 11 wherein a result from one or more features is flagged based on the retrieved performance characteristic.

13. A method according to claim 11 wherein a result from one or more features is rejected based on the retrieved performance characteristic.

14. A method according to claim 11 wherein the performance characteristic comprises reader accuracy.

15. A method according to claim 11 wherein the performance characteristic comprises reader responsivity.

16. A method according to claim 12 wherein the performance characteristic comprises reader channel cross-talk.

17. A computer program product comprising a computer readable medium carrying a computer program which executes a method of claim 1.

18. A computer program product comprising a computer readable medium carrying a computer program which executes a method of claim 3.

19. A computer program product comprising a computer readable medium carrying a computer program which executes a method of claim 11.

20. A chemical array reading system comprising:
an array reader having a detector;
a memory;
a processor unit which receives results from reading an array from the array reader and which executes a method of claim 1.

21. A chemical array reading system comprising:
an array reader having a detector;
a memory;
a processor unit which receives results from reading an array from the array reader and which executes a method of claim 2.

22. A method comprising:
reading a chemical array on an array reader, wherein the chemical array comprises biopolymer features and was exposed to a sample, and saving results of the reading in a memory wherein the results are linked with a performance characteristic of the array reader which performed the reading; or retrieving from a memory the results from reading an array and a performance characteristic of a reader which performed the reading, the results being linked with the performance characteristic and wherein the array comprises biopolymer features and was exposed to a sample; and, based on said processing, a human user who is interpreting the results of the reading assesses whether one or more targets is present in the sample or whether an organism from which the sample was obtained exhibits a particular condition, wherein the performance characteristic comprises one or more of a reader accuracy in detected signal or ratios of detected signals in different channels, a reader responsivity, or a physical characteristic of an array being read selected from the group consisting of flatness characteristics of any sample used to measure the variations of detected signal value per actual signal value over a space to be read or the flatness of the array being read.

23. A method comprising:

reading a chemical array on an array reader, wherein the chemical array comprises biopolymer features and was exposed to a sample and wherein the reader detects light emitted in response to illumination, and saving results of the reading in a memory wherein the results are linked with a performance characteristic of the array reader which performed the reading and processing the saved results using the linked performance characteristic; or retrieving from a memory the results from reading an array and a performance characteristic of a reader which performed the reading, the results being linked to the performance characteristic and processing the retrieved results using the retrieved performance characteristic, wherein the array comprises biopolymer features and was exposed to a sample; and, based on said processing, a human user who is interpreting the results of the reading assesses whether one or more targets is present in the sample or whether an organism from which the sample was obtained exhibits a particular condition, wherein the performance characteristic comprises one or more of a reader accuracy, a reader responsivity or reader channel cross-talk and wherein processing includes rejecting or flagging as suspect a result from one or more features based on a predetermined performance characteristic or generating error bars or confidence intervals for a result from one or more features.

* * * * *